(12) United States Patent
Vostrikov et al.

(10) Patent No.: US 11,698,676 B2
(45) Date of Patent: Jul. 11, 2023

(54) METHOD AND ELECTRONIC DEVICE FOR EYE-TRACKING

(71) Applicant: Samsung Electronics Co., Ltd., Suwon-si (KR)

(72) Inventors: Gavril Nikolaevich Vostrikov, Moscow region (RU); Nikolay Victorovich Muravev, Moscow region (RU); Dmitriy Evgenyevich Piskunov, Moscow region (RU); Mikhail Vyacheslavovich Popov, Moscow region (RU)

(73) Assignee: Samsung Electronics Co., Ltd., Suwon-si (KR)

( * ) Notice: Subject to any disclaimer, the term of this patent is extended or adjusted under 35 U.S.C. 154(b) by 303 days.

(21) Appl. No.: 16/996,203

(22) Filed: Aug. 18, 2020

(65) Prior Publication Data

US 2021/0055792 A1    Feb. 25, 2021

(30) Foreign Application Priority Data

Aug. 23, 2019  (RU) ............................ RU2019126697
May 21, 2020  (KR) ........................ 10-2020-0060900

(51) Int. Cl.
  *G06F 3/01*      (2006.01)
  *G01B 11/26*     (2006.01)
  *G06V 40/18*     (2022.01)

(52) U.S. Cl.
  CPC .............. *G06F 3/013* (2013.01); *G01B 11/26* (2013.01); *G06F 3/011* (2013.01); *G06V 40/18* (2022.01)

(58) Field of Classification Search
  CPC ......... G06F 3/013; G06F 3/011; G06V 40/18; G01B 11/26
  See application file for complete search history.

(56) References Cited

U.S. PATENT DOCUMENTS

| 10,027,883 B1 | 7/2018 | Kuo et al. |
| 10,213,105 B2 | 2/2019 | Sarkar |
| 10,228,558 B2 | 3/2019 | Aleem et al. |
| 10,257,507 B1 | 4/2019 | Trail |

(Continued)

FOREIGN PATENT DOCUMENTS

| KR | 10-2013-0118897 A | 10/2013 |
| RU | 2 487 653 C2 | 2/2013 |

(Continued)

OTHER PUBLICATIONS

Russian Search Report dated Feb. 3, 2020, issued in Russian Patent Application No. 2019126697/14(052379).

(Continued)

*Primary Examiner* — Afroza Chowdhury
(74) *Attorney, Agent, or Firm* — Jefferson IP Law, LLP

(57) ABSTRACT

An eye-tracking electronic device is provided. The eye-tracking electronic device includes a scanner, at least two photodetectors configured to generate electric pulses when a scanning line reflected from a cornea is incident thereon, and at least one processor configured to generate at least one scanning line through the scanner, radiate the at least one scanning line to the cornea, and determine a direction of gaze based on time information when the at least two photodetectors generate the electrical pulses.

15 Claims, 16 Drawing Sheets

(56) References Cited

U.S. PATENT DOCUMENTS

| | | | |
|---|---|---|---|
| 10,303,248 B2 | 5/2019 | Gibson et al. | |
| 2016/0161754 A1 | 6/2016 | Hyodo et al. | |
| 2017/0255012 A1* | 9/2017 | Tam | G02B 27/0179 |
| 2017/0276934 A1 | 9/2017 | Sarkar | |
| 2018/0210547 A1 | 7/2018 | Sarkar | |
| 2018/0314325 A1* | 11/2018 | Gibson | G06V 40/19 |
| 2019/0050051 A1 | 2/2019 | Cirucci et al. | |
| 2019/0056599 A1 | 2/2019 | Reshidko et al. | |
| 2020/0227048 A1 | 7/2020 | Rodriguez et al. | |

FOREIGN PATENT DOCUMENTS

| | | |
|---|---|---|
| RU | 2 625 815 C2 | 3/2017 |
| RU | 2 665 289 C1 | 8/2018 |

OTHER PUBLICATIONS

Russian Decision to Grant dated May 19, 2020, issued in Russian Patent Application No. 2019126697/14(052379).

\* cited by examiner

METHOD AND ELECTRONIC DEVICE FOR EYE-TRACKING

CROSS-REFERENCE TO RELATED APPLICATION(S)

This application is based on and claims priority under 35 U.S.C. § 119(a) of a Russian patent application number 2019126697, filed on Aug. 23, 2019, in the Russian Patent Office, and of a Korean patent application number 10-2020-0060900, filed on May 21, 2020, in the Korean Intellectual Property Office, the disclosure of each of which is incorporated by reference herein in its entirety.

BACKGROUND

1. Field

The disclosure relates to a method and an electronic device for eye-tracking. More particularly, the disclosure relates to determining the direction of the gaze based on a time when the electric pulses are generated respectively by the at least two photodetectors and a generation time interval.

2. Description of Related Art

In recent years, most eye-tracking sensors use cameras. Camera sensors perform many calculations to determine the pupil position in an image. Therefore, calculation processing elements and cameras in electronic devices take up a lot of space and consume a lot of power. In addition, eye-tracking using a camera sensor has limitations in accuracy and frequency of the update rate. Therefore, a camera sensor is not suitable for electronic devices such as virtual reality (VR) and augmented reality (AR) systems. Because microelectromechanical system (MEMS) sensors are compact and have smaller power consumption, a next-generation of eye-tracking sensors based on MEMS scanners are being developed.

In a method for resonant eye-tracking disclosed in US Patent Application Publication No. 2018/0210547, a beam of light is steered through a MEMS scanner operating at a resonant frequency and light reflected from an eye surface is detected. However, this method for resonant eye-tracking has low accuracy in determining the position of the eyes and requires a two-axis MEMS scanner when frequency of the update rate is low.

Eye tracking using scanned beam and multiple detectors disclosed in U.S. Pat. No. 10,303,248 includes an infrared light source, scanning optics configured to scan light from the infrared light source across a region comprising a user's cornea, and a plurality of photodetectors, each photodetector being configured to detect infrared light reflected from the user's cornea at a corresponding angle. The eye tracking using scanned beam and multiple detectors also has drawbacks that accuracy in determining the position of the eyes is low and a two-axis MEMS scanner is required when frequency of the update rate is low.

The eye-tracking system and method therefor disclosed in U.S. Pat. No. 10,213,105 B2 includes a point light source, a two-coordinate scanning MEMS mirror that has an ability to rotate along two-coordinate axes, and a photodetector. Light from the point light source is radiated towards the scanner, is reflected from the scanner, and scans the area where the cornea of the eye is located. The photodetector captures the light reflected from the cornea of the eye at different points of time. The position of the cornea is then calculated by analyzing the amplitude of a signal of the photodetector, which detected the reflected light at different points in time. The time between the intensity maximum during a sweep is indicative of the position of the cornea within the eye surface. The disadvantages of the eye-tracking system and method therefor are low accuracy of detecting the position of the eyes, low frequency of updating information, and use of a two-axis scanner. In addition, it is necessary to create a line-frame scan and to analyze a signal amplitude, which complicates the process of determining the position of the eyes, increases measurement errors, and reduces the frequency of updating information.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a method and an electronic device for eye-tracking.

Additional aspects will be set forth in part in the description which follows and, in part, will be apparent from the description, or may be learned by practice of the presented embodiments.

In accordance with an aspect of the disclosure, an eye-tracking electronic device is provided. The eye-tracking electronic device includes a scanner, at least two photodetectors configured to generate electric pulses when a scanning line reflected from a cornea is incident thereon, and at least one processor configured to generate at least one scanning line through the scanner, radiate the at least one scanning line to the cornea, and determine a direction of a gaze based on time information when the at least two photodetectors generate the electrical pulses.

The scanner may include a light source configured to generate the at least one scanning line, and an optical element configured to convert the at least one scanning line to form a scanning area of a linear shape perpendicular to a scanning direction.

The light source and the optical element may each rotate around at least one axis.

The scanner may further include a scanner mirror configured to reflect the converted at least one scanning line and rotate around at least one axis.

The determining of the direction of the gaze may include determining an angle of a position of the cornea.

The at least one processor may digitalize the electric pulses and determine the direction of the gaze based on time information when the digitalized electric pulses are generated.

The at least one processor may digitalize the electric pulses by comparing the electric pulses with a set reference value.

The at least one processor may determine the direction of the gaze based on a time when the electric pulses are generated respectively by the at least two photodetectors and a generation time interval.

The at least one processor may determine the direction of the gaze based on a scanning speed of the scanner.

In accordance with another aspect of the disclosure, a method, performed by an eye-tracking electronic device, of determining a direction of a gaze is provided. The method includes generating, by a scanner, at least one scanning line, radiating the at least one scanning line to a cornea, at least two photodetectors generating electric pulses when the at least one scanning line is reflected from the cornea and is incident thereon, and determining the direction of a gaze based on time information when the electrical pulses are generated.

The generating of the at least one scanning line may include converting the at least one scanning line to form a scanning area of a linear shape perpendicular to a scanning direction.

The scanner may include a light source and an optical element each configured to rotate around at least one axis.

The scanner may further include a scanner mirror configured to reflect the converted at least one scanning line and rotate around at least one axis.

The determining of the direction of the gaze may include determining an angle of a position of the cornea.

The determining of the direction of the gaze based on the time information when the electrical pulses are generated may include digitalizing the electric pulses and determining the direction of the gaze based on the time information when the digitalized electric pulses are generated.

The digitalizing of the electric pulses may include digitalizing the electric pulses by comparing the electric pulses with a set reference value.

The determining of the direction of the gaze based on the time information at which the electrical pulses are generated may include determining the direction of the gaze based on a time when the electric pulses are generated respectively by the at least two photodetectors and a generation time interval.

The determining of the direction of the gaze based on the time information when the electrical pulses are generated may include determining the direction of the gaze based on a scanning speed of the scanner.

In accordance with another aspect of the disclosure, a non-transitory computer-readable recording medium having recorded thereon a program for executing a method, performed by an eye-tracking electronic device, of determining a direction of a gaze is provided. The computer program product includes generating, by a scanner, at least one scanning line, radiating the at least one scanning line to a cornea, generating, by at least two photodetectors, electric pulses when the at least one scanning line is reflected from the cornea and is incident thereon, and determining the direction of the gaze based on time information when the electrical pulses are generated.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
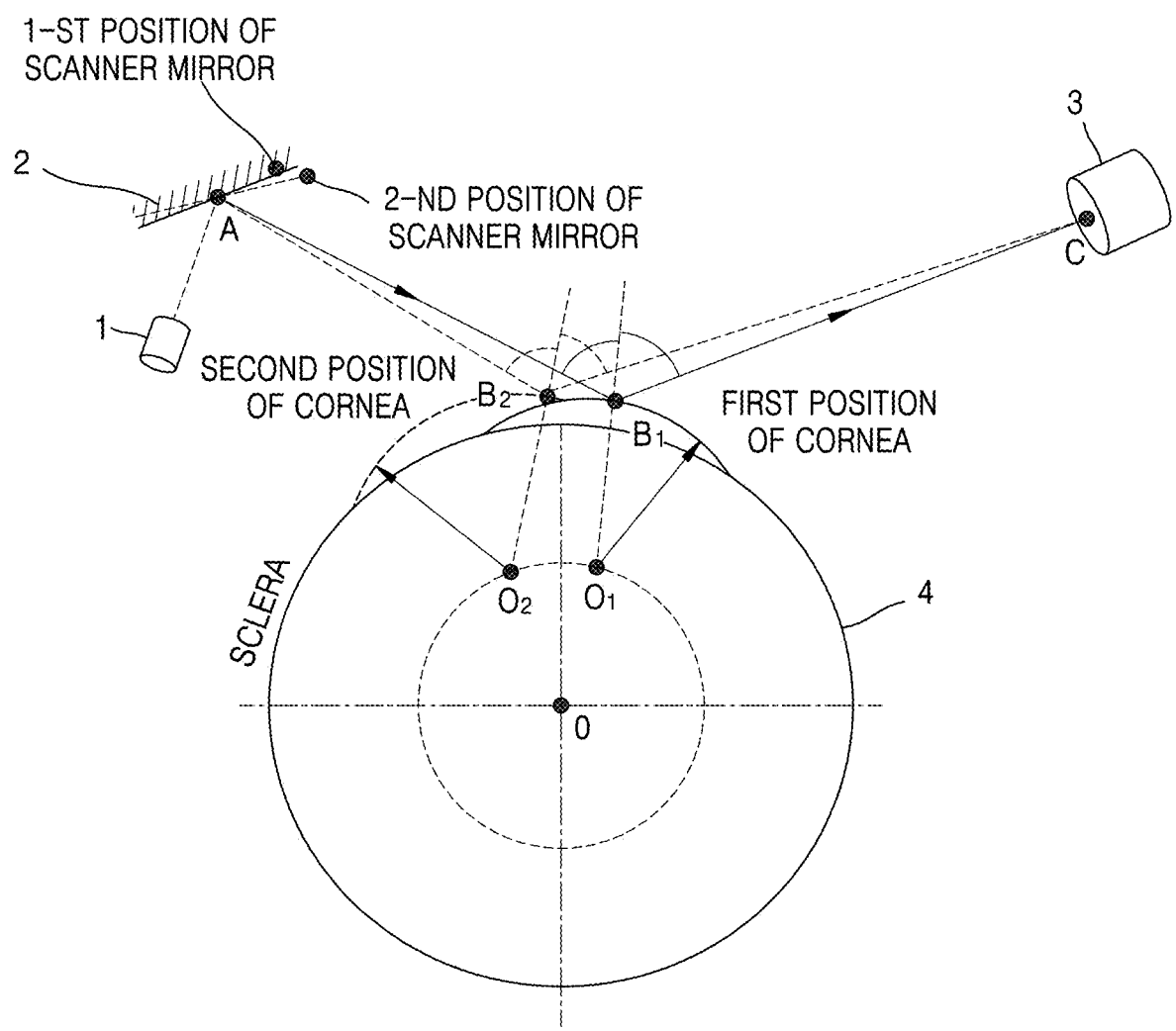
FIG. 1 is a diagram illustrating an operation by which an electronic device determines an eye position according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Although the terms used in the disclosure have been described in general terms that are currently used in consideration of the functions referred to in the disclosure, the terms are intended to encompass various other terms depending on the intent of those skilled in the art, precedents, or the emergence of new technology. Also, some of the terms used herein may be arbitrarily chosen by the applicant. In this case, these terms are defined in detail below. Accordingly, the terms used in the disclosure are not defined based on the meaning of the term, not on the name of a simple term, but on the contents throughout the disclosure.

The terms including technical and scientific terms used herein have the same meaning as commonly understood by one of ordinary skill in the art to which the disclosure belongs.

Throughout the entirety of the specification of the disclosure, when it is assumed that a certain part includes a certain element, the term 'including' means that a corresponding element may further include other elements unless a specific meaning opposed to the corresponding element is written.

Throughout the disclosure, the expression "at least one of a, b or c" indicates only a, only b, only c, both a and b, both a and c, both b and c, all of a, b, and c, or variations thereof.

Like reference numerals denote like elements throughout the specification. This specification does not describe all elements of the embodiments of the disclosure, and redundancies between the general content in the art to which the embodiments of the disclosure pertain, known technologies, or embodiments of the disclosure are omitted.

FIG. 1 is a diagram illustrating an operation by which an electronic device determines an eye position according to an embodiment of the disclosure.

Referring to FIG. 1, an eye 4 has a center (e.g., a coordinate O) of rotation, wherein centers O1 and O2 of the cornea rotates around the center of eye rotation. A point A is the point on a scanning mirror 2 from which light is reflected. A point B1 is a first cornea position, in which the light reflected from the scanning mirror 2 is received. A point B2 is a second cornea position, in which the light reflected from the scanning mirror 2 is received. A point C is the center of the photosensitive area of a photodetector 3.

A light source 1 emits infrared radiation. An optical element (not shown) of the light source 1 converts the emitted infrared radiation. After the infrared radiation is converted, the converted infrared radiation is reflected from the scanning mirror 2 into the cornea area. The photodetector 3 is located at a certain distance from the scanning mirror 2, and the location of the photodetector 3 relative to the scanning mirror 2 is determined at the time of design. That is, the location of the photodetector 3 relative to the scanning mirror 2 may be used with a given value without additional calculation.

The photodetector 3 generates an electric pulse at a time when the converted infrared radiation reflected from the cornea falls on the photodetector 3. That is, the photodetector 3 generates an electric signal. The maximum value of the electric signal is generated when an angle $AB_1O_1$ of incidence of the converted infrared radiation onto the cornea is equal to an angle $O_1B_1C$ of reflection of the converted infrared radiation from the cornea. In this case, the point C which is the center of the photosensitive area of a photodetector 3, the point A in which the converted infrared radiation is reflected from the scanning mirror 2, the point $B_1$ which is the first cornea position in which the reflected and converted infrared radiation is received and a center $O_1$ of the cornea lie in the same plane.

When the eyeball rotates (i.e., the cornea moves to $B_2$ and the center of the cornea rotates to a point $O_2$), the maximum value of the electric signal of the photodetector 3 is generated at a different time from the corona position $B_1$ because an angle $AB_2O_2$ of incidence of the converted infrared radiation onto the cornea is equal to an angle $O_2B_2C$ of reflection of the converted infrared radiation from the cornea and the points A, $B_2$, $O_2$, and C are in the same plane.

It should be noted that in the absence of the converted infrared radiation reflected from the cornea on the photodetector 3, a significantly less amount of the converted infrared radiation is incident because the converted infrared radiation reflected (or scattered) from other elements of the eye excluding the cornea may be incident on the photodetector 3.

The converted infrared radiation may be reflected and scattered from all elements of the eye. However, the strongest infrared radiation among the converted infrared radiation is reflected, and in the structure of the eye, the cornea reflects the strongest signal. Therefore, the maximum value of the electric signal is generated by the photodetector 3 when the converted infrared radiation is reflected from the cornea.

The scanner may be a system including a light source, an optical element forming a scanning trajectory and a rotating scanner that reflects the scanning trajectory in the direction of the eye. It is advisable to use infrared radiation or light emitting diode (LED) as the light source.

In another case, the scanner may be a system including a light source, an optical element, and a drive. Scanning of the cornea is carried out by rotating the light source together with the optical element around one axis. The optical element should form an illumination region in the eye area in the form of a line perpendicular to the scanning direction (scanning trajectory). In this case, scanning is performed using the drive that rotates the light source and the optical element such that the light source and the optical element rotate uniformly, first in one direction and then in the opposite direction. The drive may be a microelectromechanical system (MEMS) device or a compact electromechanical drive.

Figure 2:
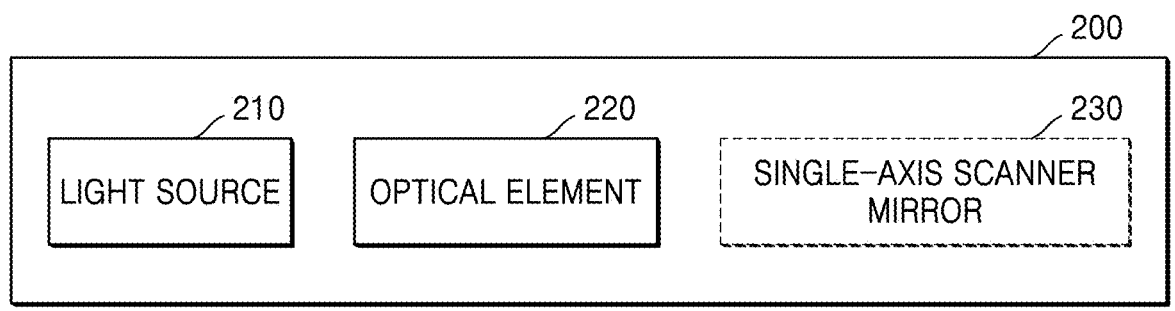
FIG. 2 is a diagram illustrating a scanner of an eye-tracking electronic device according to an embodiment of the disclosure.

FIG. 2 is a diagram illustrating a scanner of an eye-tracking electronic device according to an embodiment of the disclosure.

Referring to FIG. 2, a scanner 200 may include a light source 210 and an optical element 220. Alternatively, the scanner 200 may include a single-axis scanner mirror 230.

The light source 210 generates at least one scanning line. The scanning line may be radiated with infrared rays.

The optical element 220 may convert the scanning line to form various types of scanning areas. For example, the optical element 220 converts the scanning line to form a scanning area in the form of a line perpendicular to the scanning direction. The scanning area completely scans the eye by passing from the inner corner of the eye (which is the nose direction) to the outer corner of the eye (which is in the ear direction) (or vice versa). As described above, the scanning area completely scans the eye by passing from the inner corner of the eye to the outer corner of the eye, thereby more accurately determining the angle of the cornea position by preventing the occurrence of shading caused by the eyelid.

In addition, the scanning area in the form of a line having a length from the upper eyelid to the lower eyelid rather than a point scans the eye completely, thereby more quickly and accurately updating the direction of gaze.

In an embodiment of the disclosure, the light source 210 and the optical element 220 may rotate around at least one axis. Accordingly, the scanner 200 may completely scan the eye by moving the scanning area through rotation of the light source 210 and the optical element 220.

In another embodiment of the disclosure, the scanner 200 may include the single-axis scanner mirror 230. The single-axis scanner mirror 230 may rotate around one axis and reflect the scanning line converted by the optical element 220 in the direction of the cornea. The scanner 200 may completely scan the eye by moving the scanning area by moving the scanning area through rotation of the single-axis scanner mirror 230. When the scanner 200 includes the single-axis scanner mirror 230, the light source 210 and the optical element 220 may not rotate.

Figure 3:
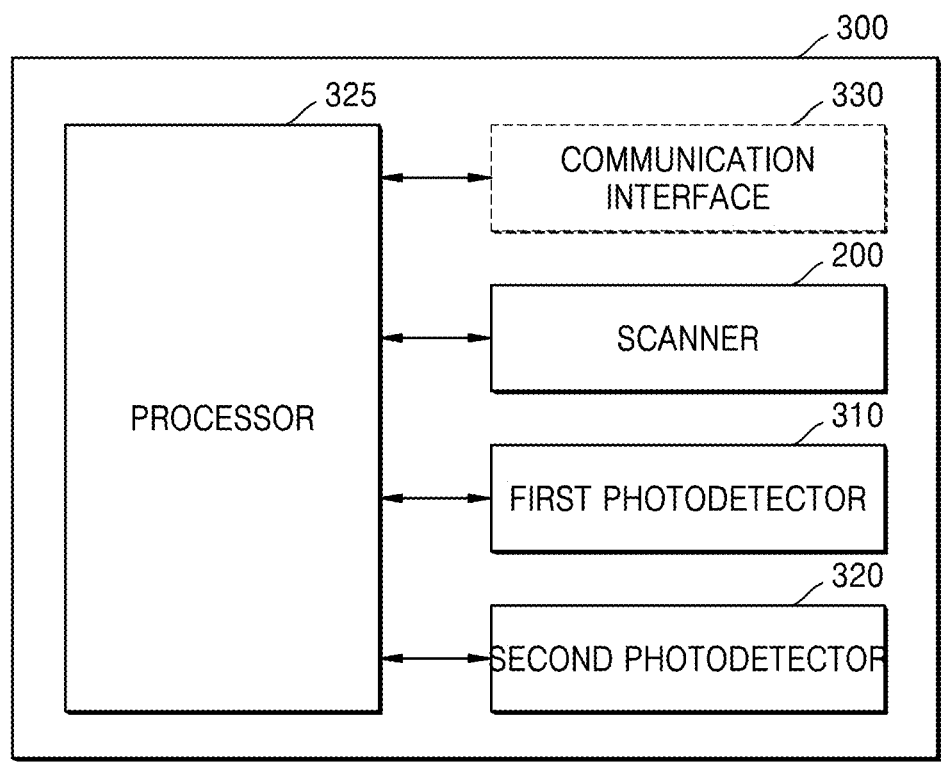
FIG. 3 is a diagram illustrating an eye-tracking electronic device according to an embodiment of the disclosure.

FIG. 3 is a diagram illustrating an eye-tracking electronic device according to an embodiment of the disclosure. The redundant configuration with FIG. 2 is briefly described.

Referring to FIG. 3, an eye-tracking electronic device 300 may be a virtual reality system, an augmented reality system, an ophthalmic medical device, etc. The eye-tracking electronic device 300 may also be applied to a viewfinder of a camera for a function of determining a focal point from the pupil's position. The disclosure is not limited to thereto.

The eye-tracking electronic device 300 includes the scanner 200, at least two photodetectors 310 and 320, and a processor 325. In addition, the eye-tracking electronic device 300 may selectively include a communication interface 330.

As described above, the scanner 200 may include the light source 210 and the optical element 220. In addition, the scanner 200 may move the scanning area through the rotation of the light source 210 and the optical element 220 or through the rotation of the single-axis scanner mirror 230.

According to an embodiment of the disclosure, each of the photodetectors 310 and 320 may generate an electric pulse when a scanning line reflected from the cornea is incident. The position of each of the photodetectors 310 and 320 may be determined at the time of design. Also, the positions of the photodetectors 310 and 320 may be separated from each other.

An angle of reflection of the scanning line in the cornea in which each of the photodetectors 310 and 320 generates the electrical pulse is determined based on the position of the cornea. Because the scanning line satisfies the law of reflection and is reflected from the cornea, the angle of incidence of the scanning line in the cornea is determined. At this time, because the positions of the photodetectors 310 and 320 are different, the angle of incidence (or reflection) of the scanning line in the cornea may be different.

The angle of incidence of the scanning line is determined by the angle of rotation of the scanner 200. Therefore, each of the photodetectors 310 and 320 may detect a scanning line incident at the angle of rotation of the scanner 200 according to the position of the cornea.

In another embodiment of the disclosure, the number of photodetectors 310 and 320 in the eye-tracking electronic device 300 increases, thereby increasing the range for detecting the angle of rotation of the scanner 200 and more accurately determining the angle of the corneal position.

As described above, each of the photodetectors 310 and 320 may detect a scanning line incident at a specific angle of rotation of the scanner 200 that satisfies the law of reflection. Accordingly, when the angles of rotation of the scanner 200 detected by the photodetectors 310 and 320 are used in combination with each other, information about the direction of the gaze may be obtained in one scan (or one period). That is, the frequency of updating information about the direction of the gaze may increase and the direction of the gaze may be more accurately determined.

In some cases, the scanning line in the cornea may be partially reflected by being refracted or scattered. That is, all scanning lines reflected from the cornea may not be incident on the photodetectors 310 and 320. Therefore, because it is difficult to determine the direction of the gaze based on the intensity of the electric pulses generated by the photodetectors 310 and 320, there is a need to determine the direction of the gaze (including the angle of the cornea position) based on the generation time information of the electric pulse.

The processor 325 may control the overall operation of the eye-tracking electronic device 300. For example, the processor 325 may generally control the scanner 200 or the photodetectors 310 and 320 by executing programs stored in a memory (not shown). The processor 325 may include one or more processors.

The processor 325 may generate at least one scanning line through the scanner 200, radiate the scanning line to the cornea, and change the scanning direction. In addition, the processor 325 may determine the direction of the gaze based on the generation time information of the electric pulses in the photodetectors 310 and 320. Determining the direction of the gaze includes determining the angle at which the cornea rotates. In this regard, the operation of the processor 325 to determine the angle of the cornea position will be described in detail with reference to FIGS. 10 to 13.

The direction of the gaze may be used for user interfaces, for selecting virtual content elements, for automatically scrolling for reading, for selecting directions, entering text, recognizing the physiological state of the user by eye movement parameters, etc.

In another embodiment of the disclosure, the eye-tracking electronic device 300 may include a communication interface 330. The eye-tracking electronic device 300 may determine the direction of the gaze by the processor 325 and transmit the direction of the gaze to an external electronic device (not shown) through the communication interface 330. The external electronic device (not shown) may determine the direction of view using the direction of the gaze. For example, when the external electronic device (not shown) is a VR or an AR device, the external electronic device (not shown) may display only information in the direction of the gaze, that is, information present in the field of view.

Figure 4:
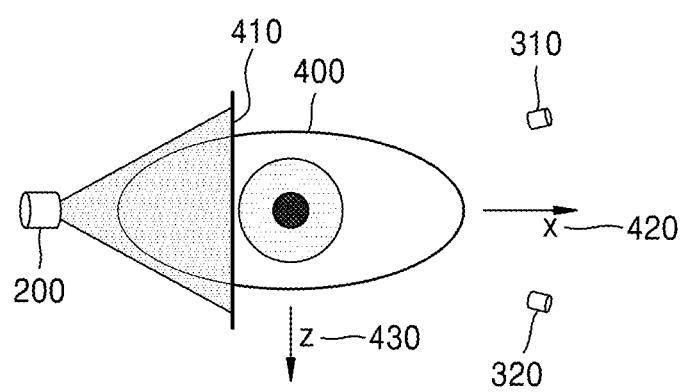
FIG. 4 is a diagram illustrating an eye-tracking electronic device that is operating according to an embodiment of the disclosure.

FIG. 4 is a diagram illustrating an eye-tracking electronic device that is operating according to an embodiment of the disclosure.

Referring to FIG. 4, the redundant configuration with FIG. 3 is briefly described.

The scanner 200 may include the light source 210 and the optical element 220. In addition, the scanner 200 may move a scanning area 410 through the rotation of the light source 210 and the optical element 220 or through the rotation of the single-axis scanner mirror 230. The photodetectors 310 and 320 may generate electric pulses when a scanning line reflected from the cornea is incident.

The position of an eye 400 may be expressed mathematically. For example, the position of the eye 400 may be mathematically expressed through an angle of rotation around an x-axis 420 and/or a z-axis 430. This will be described in detail with reference to FIG. 9.

The scanning direction is determined by the direction of rotation of the light source 210 and the optical element 220 or the direction of rotation of the single-axis scanner mirror 230. For example, the scanning direction may be a positive or negative direction of the x-axis 420.

The scanning area 410 may be in the linear shape perpendicular to the scanning direction. For example, when the scanning direction is the positive or negative direction of the x-axis 420, the scanning area 410 may be in the linear shape in the z-axis 430 direction perpendicular to the x-axis 420.

Figure 5:
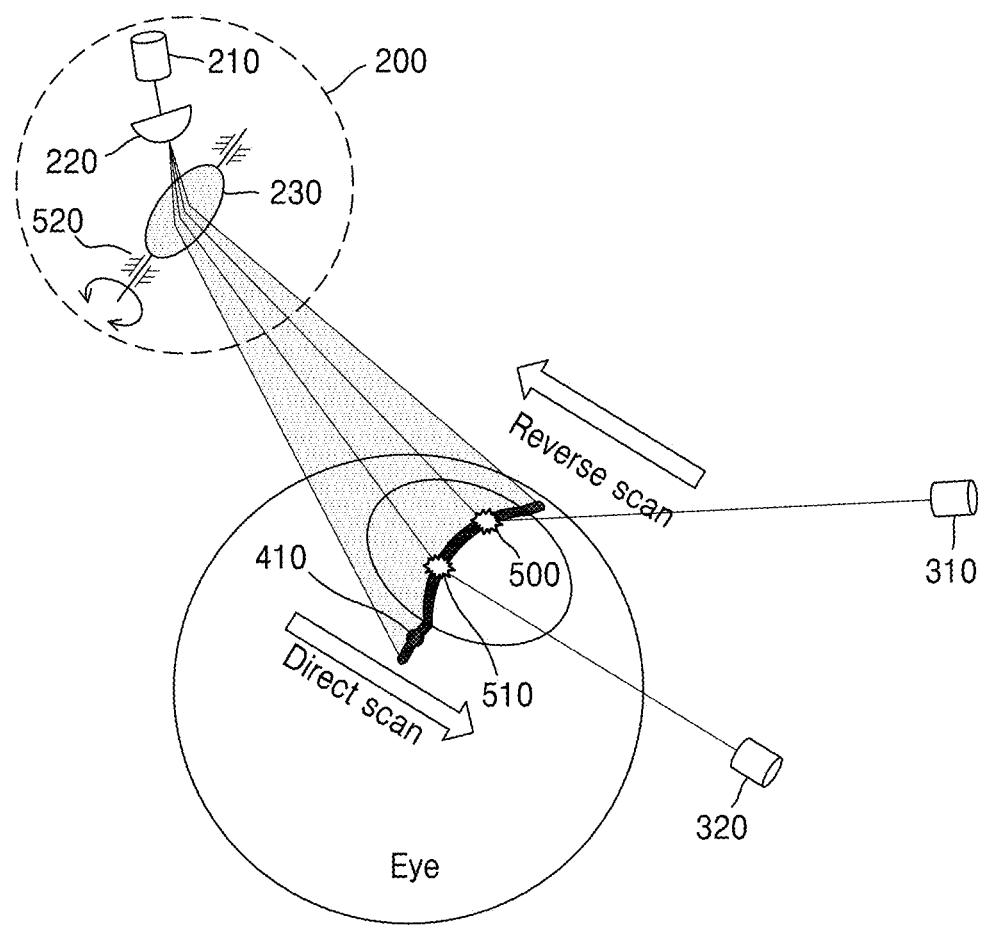
FIG. 5 is a diagram for describing a scanning line incident on photodetectors according to an embodiment of the disclosure.

FIG. 5 is a diagram for describing a scanning line incident on photodetectors according to an embodiment of the disclosure.

Referring to FIG. 5, the redundant configuration with FIG. 4 is briefly described.

The scanner 200 may include the light source 210, the optical element 220, and the single-axis scanner mirror 230.

The light source 210 generates at least one scanning line.

The optical element 220 converts the scanning line to form the scanning area 410 in the form of a line perpendicular to the scanning direction (e.g., REVERSE SCAN).

The single-axis scanner mirror 230 reflects the converted scanning line in the direction of corneas 500 and 510. Also, the single-axis scanner mirror 230 may rotate relative to one axis 520 by the processor 325 to move the scanning area 410.

The scanning line is reflected from the corneas 500 and 510 and is incident on the photodetectors 310 and 320. Among a plurality of scanning lines in the scanning area 410, only the scanning line reflected from the corneas 500 and 510 are incident on the photodetectors 310 and 320.

The photodetectors 310 and 320 may generate electric pulses when the scanning line reflected from the corneas 500 and 510 is incident. Because the law of reflection needs to be satisfied, the scanning line reflected from the cornea 500 is incident only on the first photodetector 310 and the scanning line reflected from the cornea 510 is incident only on the second photodetector 320.

Figure 6:
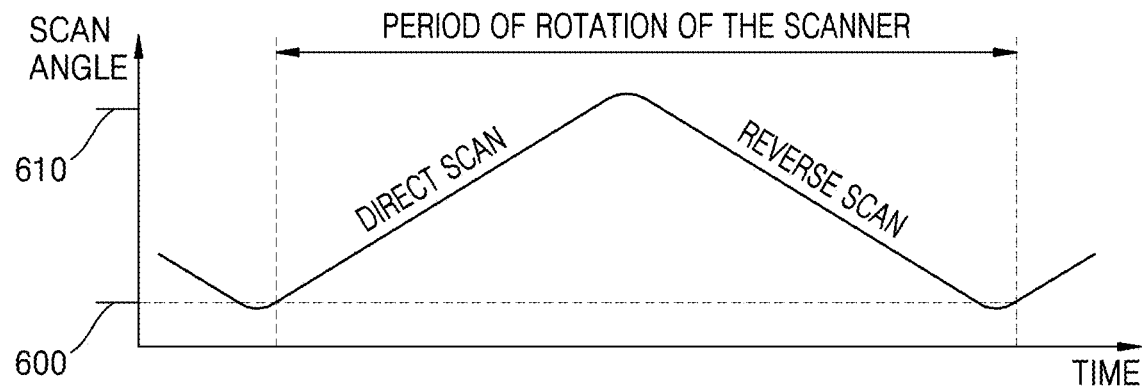
FIG. 6 is a diagram for describing a rotation of a scanner according to an embodiment of the disclosure.
Figure 7:
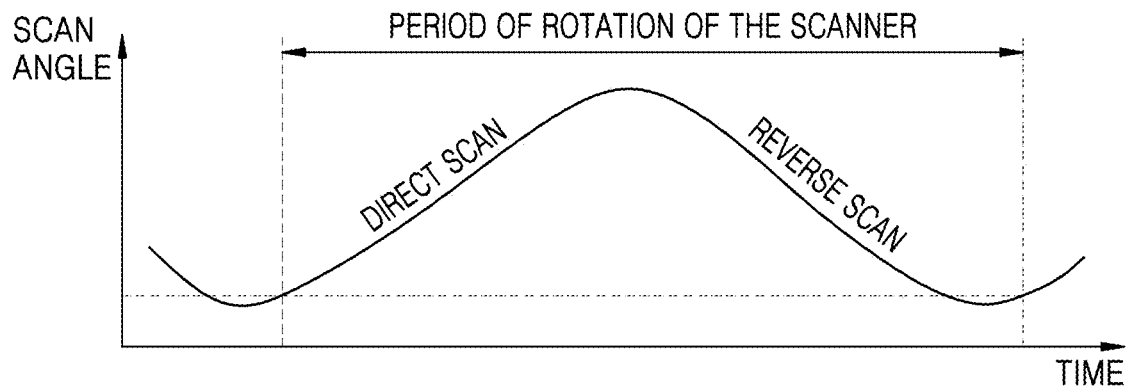
FIG. 7 is a diagram for describing a rotation of a scanner according to an embodiment of the disclosure.
Figure 8:
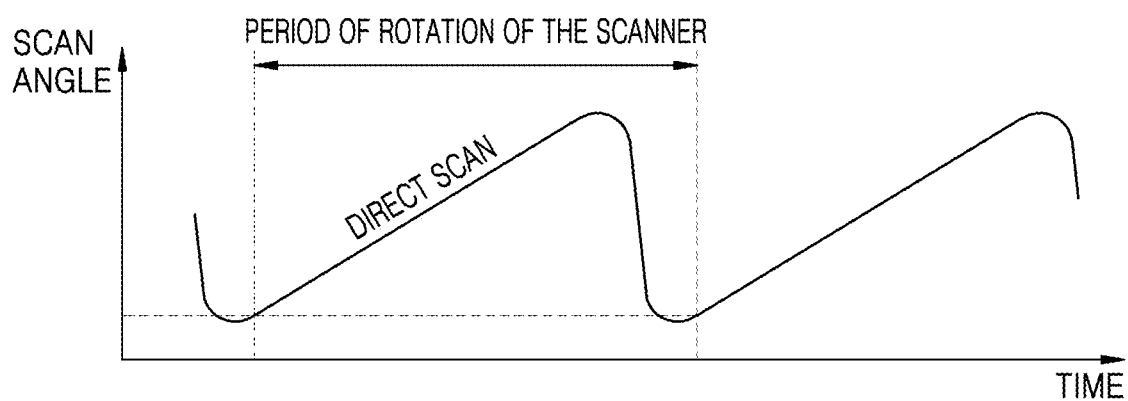
FIG. 8 is a diagram for describing a rotation of a scanner according to an embodiment of the disclosure.

FIGS. 6, 7 and 8 are diagrams illustrating a rotation of the scanner according to various embodiments of the disclosure.

The processor 325 may move a scanning area through rotation of the scanner 200. The direction of rotation of the scanner 200 may determine the scanning direction (e.g., REVERSE SCAN), and the processor 325 may control the rotation of the scanner 200.

Referring to FIG. 6, the processor 325 may linearly increase (or decrease) the angle of rotation of the scanner 200 over time. That is, the processor 325 may rotate the scanner 200 at a uniform speed. In addition, the processor 325 may change the scanning direction at a start point 600 or at an end point 610 of the angle of rotation of the scanner 200. The processor 325 may determine a time when the start point 600 or the end point 610 of the angle of rotation of the scanner 200 reappears as the period of rotation of the scanner 200.

Referring to FIGS. 7 and 8, the processor 325 may non-linearly increase (or decrease) the angle of rotation of the scanner 200 over time.

That is, in FIG. 7, the processor 325 increases (or decreases) the angle of rotation of the scanner 200 over time in the form of a sinusoidal curve. At this time, the scanner 200 may operate at a resonance frequency for high scan frequency and amplitude. In addition, when the angle of rotation of the scanner 200 is the sinusoidal curve as shown in FIG. 7, the direction of the gaze, for example, the angle of the cornea position, should be determined in consideration of the nonlinear properties of the sinusoidal curve.

In FIG. 8, the processor 325 increases (or decreases) the angle of rotation of the scanner 200 over time in the form of a saw tooth. At this time, the processor 325 may determine the direction of the gaze, for example, based on the electrical pulse generated when the scanner 200 scans in the forward direction to accelerate the position update of the cornea. That is, the processor 325 may ignore the electrical pulse generated when the scanner 200 scans in the reverse direction.

As described above, the processor 325 may increase (or decrease) the angle of rotation of the scanner 200 over time in various forms. Therefore, in consideration of a change in the position of the cornea, the processor 325 may accurately determine the direction of the gaze and increase the frequency of updating the direction of the gaze. For example, when the position of the cornea changes rapidly, the processor 325 rapidly increases (or decreases) the angle of rotation of the scanner 200 over time and slowly increases (or decreases) the angle of rotation of the scanner 200 near the position of the cornea, thereby quickly and accurately updating the direction of the gaze, for example, the position of the cornea.

Figure 9:
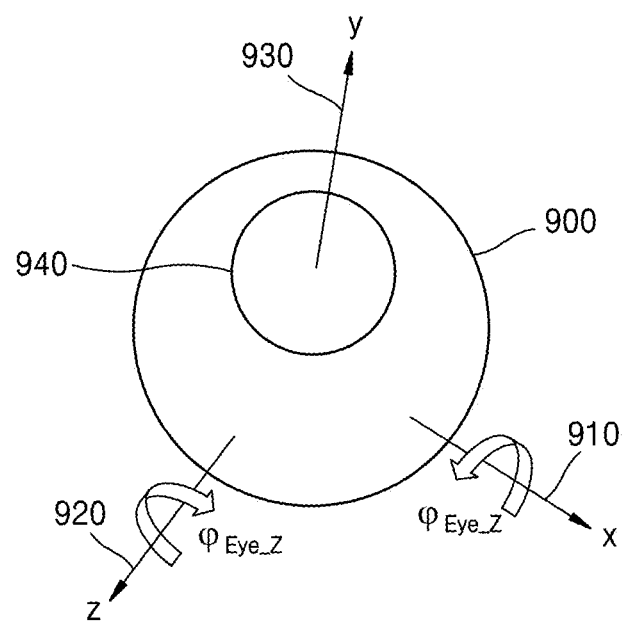
FIG. 9 is a diagram for describing mathematical modeling of a movement of an eyeball used in an eye-tracking electronic device according to an embodiment of the disclosure.

FIG. 9 is a diagram for describing a mathematical modeling of a movement of an eyeball used in an eye-tracking electronic device according to an embodiment of the disclosure.

Referring to FIG. 9, it is assumed that an eyeball 900 is a sphere. A three-dimensional coordinate system including an x-axis 910, a y-axis 930, and a z-axis 920 passing through the center of the eyeball 900 may mathematically express the movement of the eyeball 900. However, the y-axis 930 is illustrated for the convenience of understanding about the three-dimensional coordinate system, and may not be used to mathematically express the movement of the eyeball 900.

The position of a cornea 940 is determined by using a scanning line reflected from the cornea 940 by the eye-tracking electronic device. Therefore, the angle of the eye position (i.e., eye-tracking) may be expressed at an angle at which the eyeball 900 rotates with respect to the x-axis 910 and/or the z-axis 920. At this time, the position of the cornea 940 is not affected by the rotation about the y-axis 930. Therefore, the y-axis 930 may not be used to mathematically express the movement of the eyeball 900.

For example, referring to FIG. 4 for convenience of understanding, it is assumed that when a user looks only at the left or right side, that is, the position of the cornea 940 moves in the positive or negative direction on the x-axis 420 or 910. In this case, the rotation of the eyeball 900 around the x-axis 420 or 910 is fixed and the direction of the gaze, for example, the position of the cornea 940 is expressed through only the rotation of the eyeball 900 around the z-axis 430 or 920.

Figure 10:
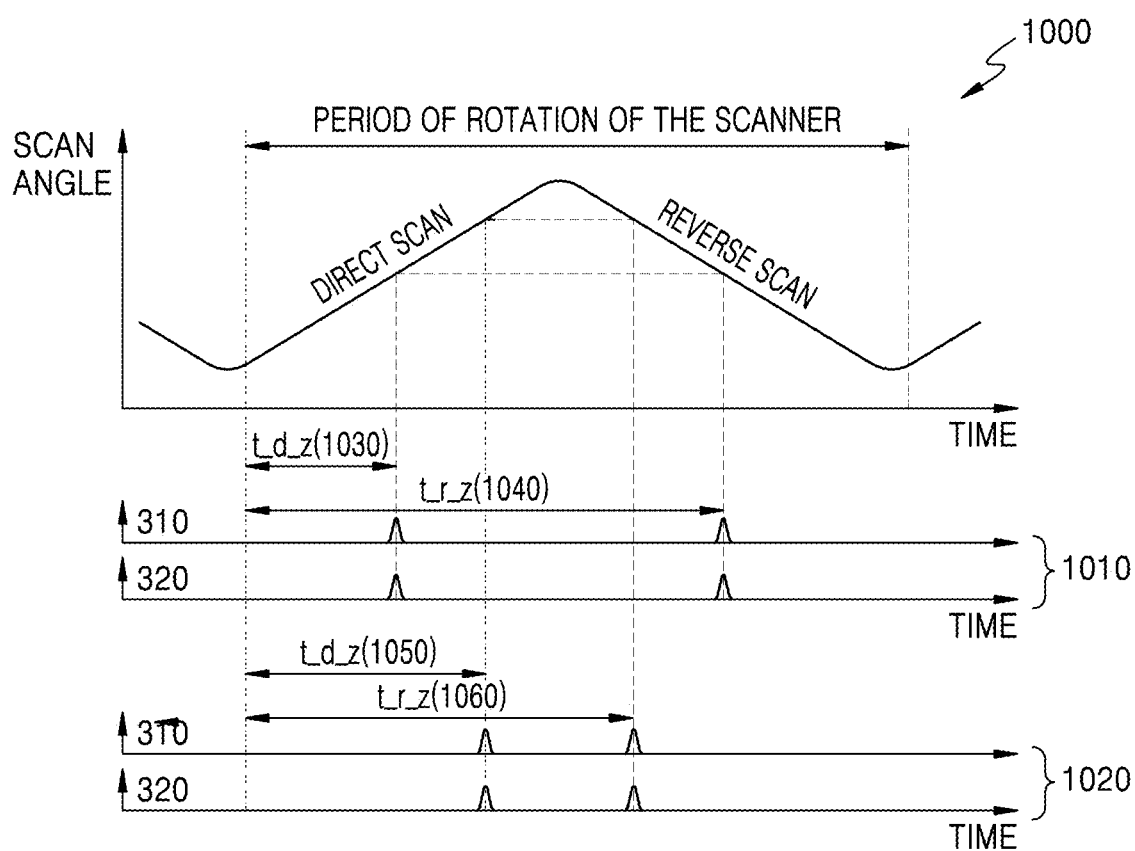
FIG. 10 is a diagram for describing an operation by which an eye-tracking electronic device determines a position of a cornea according to an embodiment of the disclosure.

FIG. 10 is a diagram for describing an operation by which an eye-tracking electronic device determines a position of a cornea according to an embodiment of the disclosure.

Referring to FIG. 10, a redundant configuration with FIG. 3 is briefly described.

The scanner 200 may include the light source 210, the optical element 220, and the single-axis scanner mirror 230.

The light source 210 generates at least one scanning line.

The optical element 220 converts the scanning line to form the scanning area 410 in the form of a line perpendicular to the scanning direction (e.g., REVERSE SCAN).

The single-axis scanner mirror 230 reflects the converted scanning line in the direction of the corneas 500 and 510. Also, the single-axis scanner mirror 230 may rotate relative to the one axis 520 by the processor 325 to linearly 1000 move the scanning area 410.

The photodetectors 310 and 320 may respectively generate electric pulses 1010 and 1020 when a scanning line reflected from the corneas is incident. The processor 325 may determine the direction of gaze based on the generation time information of the electric pulses 1010 and 1020 in the photodetectors 310 and 320. Determining the direction of the gaze includes determining the angles of positions of the corneas.

The electrical pulses 1010 and 1020 are generated by the photodetectors 310 and 320 respectively when rotation of the positions of the corneas around the x-axis is fixed, and only rotation around the z-axis occurs. That is, it is the case that the positions of the corneas move only to the left or right (the positive or negative direction of the x-axis, see FIG. 4). In addition, degrees to which the positions of the corneas move in the electric pulses 1010 and 1020 are different from each other.

t_d_z (time direct scan z-axis rotation) 1030 and 1050 mean the time when the electrical pulses 1010 and 1020 are generated in the photodetectors 310 and 320 when the scanner 200 rotates in the forward direction.

t_r_z (time reverse scan z-axis rotation) 1040 and 1060 mean the time when the electrical pulses 1010 and 1020 are generated in the photodetectors 310 and 320 when the scanner 200 rotates in the reverse direction.

The processor 325 adjusts the angle of rotation of the scanner 200, and the positions of the photodetectors 310 and 320 (or the positions of the photodetectors 310 and 320 relative to the scanner 200) are determined at the time of design. That is, the processor 325 knows the rotational speed of the scanner 200 and the positions of the photodetectors 310 and 320. The processor 325 may determine the angle of the cornea position based on t_d_z 1030 and 1050 or t_r_z 1040 and 1060 in the photodetectors 310 and 320. That is, the processor 325 may determine the angle of rotation of the z-axis of the corneas based on t_d_z 1030 and 1050 or t_r_z 1040 and 1060.

Figure 11:
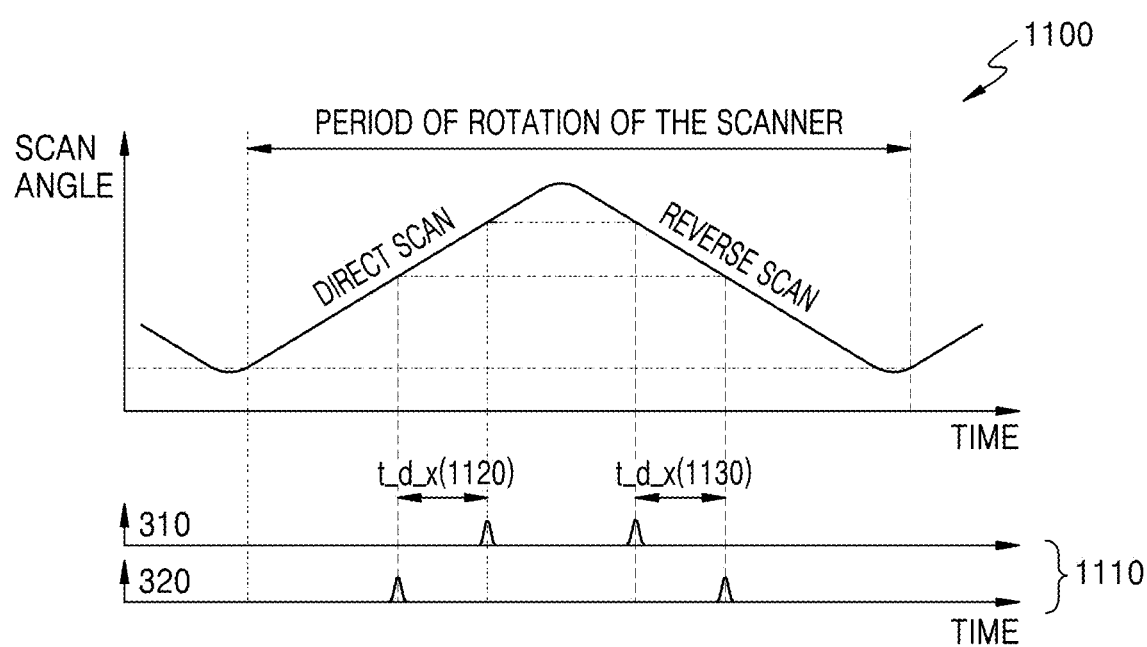
FIG. 11 is a diagram for describing an operation by which an eye-tracking electronic device determines a position of a cornea according to an embodiment of the disclosure.

FIG. 11 is a diagram for describing an operation by which an eye-tracking electronic device determines a position of a cornea according to an embodiment of the disclosure.

Referring to FIG. 11, a redundant configuration with FIG. 10 is briefly described.

The scanner 200 may include the light source 210, the optical element 220, and the single-axis scanner mirror 230.

The light source 210 generates at least one scanning line.

The optical element 220 converts the scanning line to form the scanning area 410 in the form of a line perpendicular to the scanning direction (e.g., REVERSE SCAN).

The single-axis scanner mirror 230 reflects the converted scanning line in the direction of the cornea. Also, the single-axis scanner mirror 230 may rotate relative to the one axis 520 by the processor 325 to linearly 1100 move the scanning area 410.

Each of the photodetectors 310 and 320 may generate an electric pulse 1110 when a scanning line reflected from the cornea is incident. The processor 325 may determine the direction of gaze based on the generation time information of the electric pulse 1110 in the photodetectors 310 and 320. Determining the direction of the gaze includes determining the angle of position of the cornea.

The electrical pulse 1110 is generated by each of the photodetectors 310 and 320 when rotation of the position of the cornea around the z-axis is fixed, and only rotation around the x-axis occurs. That is, it is the case that the position of the cornea moves only up or down (the positive or negative direction of the z-axis, see FIG. 4).

t_d_x (time direct scan x-axis rotation) 1120 means a time interval at which the electrical pulse 1110 is generated in each of the photodetectors 310 and 320 when the scanner 200 rotates in the forward direction.

t_r_x (time reverse scan x-axis rotation) 1130 means a time interval at which the electrical pulse 1110 is generated in each of the photodetectors 310 and 320 when the scanner 200 rotates in the reverse direction.

Each of the photodetectors 310 and 320 generates the electric pulse 1110 at a different time by the law of reflection. As the position of the cornea is higher (or lower), because the difference in the angle of rotation of the scanner 200 that satisfies the law of reflection increases, t_d_x 1120 and t_r_x 1130 increase.

The processor 325 adjusts the angle of rotation of the scanner 200, and the positions of the photodetectors 310 and 320 (or the positions of the photodetectors 310 and 320 relative to the scanner 200) are determined at the time of design. That is, the processor 325 knows the rotational speed of the scanner 200 and the positions of the photodetectors 310 and 320. The processor 325 may determine the angle of the cornea position based on t_d_x 1120 or t_r_x 1130 in the photodetectors 310 and 320. The processor 325 may determine the angle of rotation of the x-axis of the cornea based on t_d_x 1120 or t_r_x 1130.

Figure 12:
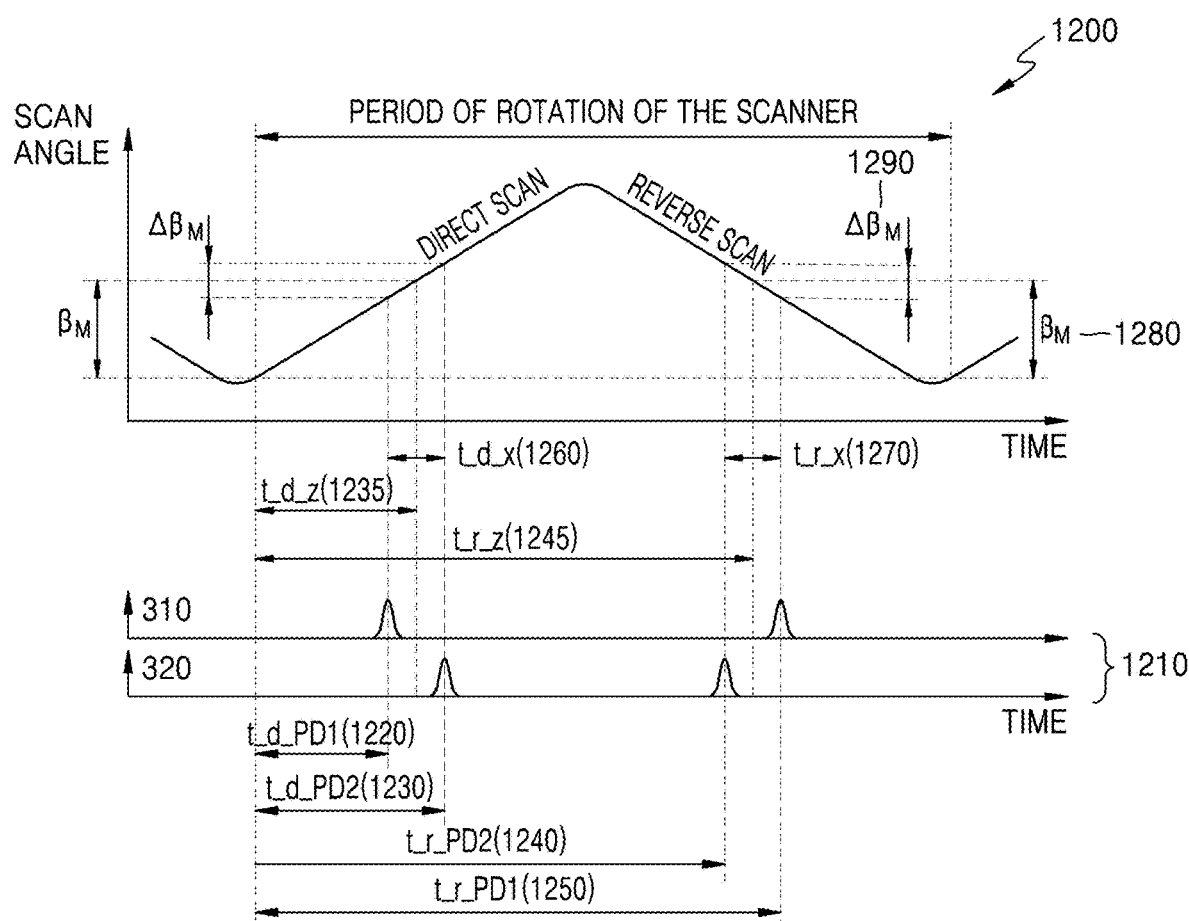
FIG. 12 is a diagram for describing an operation by which an eye-tracking electronic device determines a position of a cornea according to an embodiment of the disclosure.

FIG. 12 is a diagram for describing an operation by which an eye-tracking electronic device determines a position of a cornea according to an embodiment of the disclosure.

Referring to FIG. 12, a redundant configuration with FIG. 10 is briefly described.

The scanner 200 may include the light source 210, the optical element 220, and the single-axis scanner mirror 230.

The light source 210 generates at least one scanning line.

The optical element 220 converts the scanning line to form the scanning area 410 in the form of a line perpendicular to the scanning direction (DIRECT SCAN or REVERSE SCAN).

The single-axis scanner mirror 230 reflects the converted scanning line in the direction of the cornea. Also, the single-axis scanner mirror 230 may rotate relative to the one axis 520 by the processor 325 to linearly 1200 move the scanning area 410.

Each of the photodetectors 310 and 320 may generate an electric pulse 1210 when a scanning line reflected from the cornea is incident. The processor 325 may determine the direction of gaze based on the generation time information of the electric pulse 1210 in the photodetectors 310 and 320. Determining the direction of the gaze includes determining the angle of position of the cornea.

The electric pulse 1210 is generated by each of the photodetectors 310 and 320 when rotation of the position of the cornea occurs in the center around the x-axis and the z-axis. That is, it is the case that the position of the cornea freely moves.

t_d_PD1 (time direct rotation photodetector 1) 1220 is the time when the intensity of an electric pulse generated by the first photodetector 310 is the maximum when the scanner 200 rotates in the forward direction. Likewise, t_d_PD2 1230 is the time when the intensity of an electric pulse generated by the second photodetector 320 is the maximum.

t_r_PD1 (time reverse rotation photodetector 1) 1250 is the time when the intensity of the electric pulse generated by the first photodetector 310 is the maximum when the scanner 200 rotates in the reverse direction. Likewise, t_r_PD2 1240 is the time when the intensity of the electric pulse generated by the second photodetector 320 is the maximum.

As described above, the processor 325 may obtain t_d_PD1 1220, t_d_PD2 1230, t_r_PD1 1250, and t_r_PD2 1240 during one scanning period. Thereafter, the processor 325 may calculate Equation 1 below.

$$t\_d\_x = t\_d\_PD2 - t\_d\_PD1$$

$$t\_r\_x = t\_r\_PD2 - t\_r\_PD1$$

$$t\_d\_z = t\_d\_PD1 + t\_d\_x/2$$

$$t\_r\_z = t\_r\_PD1 + t\_r\_x/2 \quad \text{Equation 1}$$

t_d_x (time direct scan x-axis rotation) 1260 means a time interval at which the maximum intensity of the electric pulse is generated by each of the photodetectors 310 and 320 when the scanner 200 rotates in the forward direction.

t_r_x (time reverse scan x-axis rotation) 1270 means a time interval at which the maximum intensity of the electric pulse is generated by each of the photodetectors 310 and 320 when the scanner 200 rotates in the reverse direction.

As described above, t_d_x 1260 and t_r_x 1270 may be used by the processor 325 to determine the angle of x-axis rotation of the cornea.

t_d_z (time direct scan z-axis rotation) 1235 means an intermediate value of the formation time of the electric pulse generated by each of the photodetectors 310 and 320 when the scanner 200 rotates in the forward direction. That is, t_d_z 1235 means the average of the time that the maximum intensity of the electric pulse is generated by each of the photodetectors 310 and 320.

t_r_z (time reverse scan z-axis rotation) 1245 means an intermediate value of the formation time of the electric pulse generated by each of photodetectors 310 and 320 when the scanner 200 rotates in the reverse direction. That is, t_r_z 1245 means the average of the time that the maximum intensity of the electric pulse is generated by each of the photodetectors 310 and 320.

As described above, t_d_z 1235 and t_r_z 1245 may be used by the processor 325 to determine the angle of z-axis rotation of the cornea.

$\beta_M$ 1280 means an angle at which the single-axis scanner mirror 230 rotates from a start time of scanning to the intermediate value of the formation time of the electric pulse generated by each of the photodetectors 310 and 320. $\beta_M$ 1280 is determined from a pair of t_d_x 1260 and t_d_z 1235 or a pair of t_r_x 1270 and t_r_z 1245.

$\Delta\beta_M$ 1290 means an angle at which the single-axis scanner mirror 230 rotates during the time interval at which the maximum intensity of the electric pulse is generated by each of the photodetectors 310 and 320. $\Delta\beta_M$ 1290 is determined from the pair of t_d_x 1260 and t_d_z 1235 or the pair of t_r_x 1270 and t_r_z 1245.

Hereinafter, for convenience of understanding, the processor 325 rotates the single-axis scanner mirror 230 linearly 1200 but is not limited thereto.

The processor 325 may calculate Equation 2 below.

$$\Delta\beta_M = t\_d\_x \cdot \omega_{scan}$$

$$\beta_M = t\_d\_z \cdot \omega_{scan}$$

$$\Delta\beta_M = -t\_r\_x \cdot \omega_{scan}$$

$$\beta_M = (T\_scan - t\_r\_z) \cdot \omega_{scan} \quad \text{Equation 2}$$

T_scan means a scanning period. $\omega_{scan}$ means the rotation speed of the single-axis scanner mirror 230. Because the angle of rotation of the single-axis scanner mirror 230 rotates linearly 1200, a relationship that is directly proportional to $\omega_{scan}$ is established as in Equation 2 above.

The processor 325 may express $\beta_M$ 1280 and $\Delta\beta_M$ 1290 as a function of the angle of rotation of the cornea through vector algebra or numerical analysis of nonlinear equations. The processor 325 adjusts the angle of rotation of the single-axis scanner mirror 230, and the position of the photodetectors 310 and 320 (or the positions of the photodetectors 310 and 320 relative to the scanner 200) is determined at the time of design. Accordingly, the processor 325 may express $\beta_M$ 1280 and $\Delta\beta_M$ 1290 as a function of the angle of rotation of the cornea based on the positions of the photodetectors 310 and 320.

Figure 13:
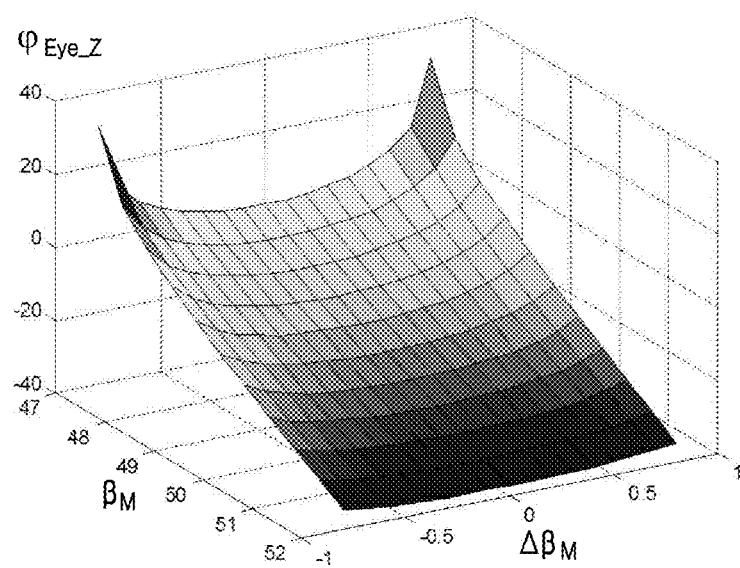
FIG. 13 is a diagram for describing an example in which an eye-tracking electronic device determines a position of a cornea according to an embodiment of the disclosure.
Figure 13:
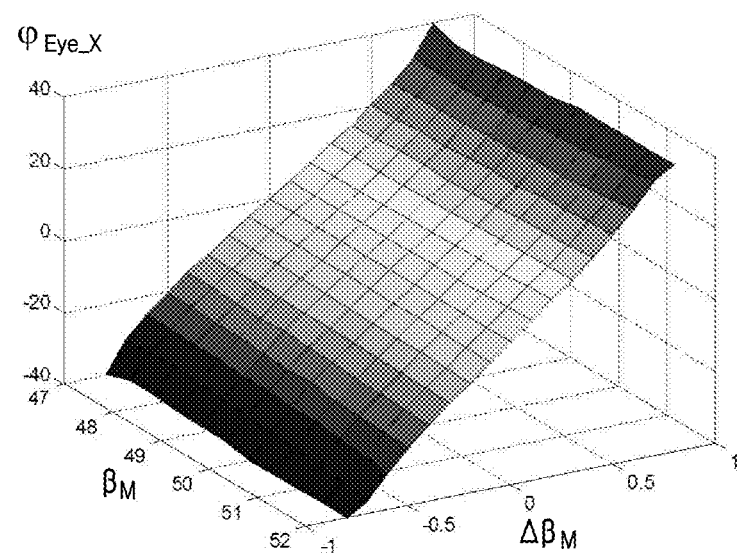

FIG. 13 is a diagram for describing an example in which an eye-tracking electronic device determines a position of a cornea according to an embodiment of the disclosure. A redundant operation with FIG. 12 is briefly described.

Referring to FIG. 13, the processor 325 may express $\beta_M$ 1280 and $\Delta\beta_M$ 1290 as a function of angles $\varphi_{Eye\_X}$ and $\varphi_{Eye\_Z}$ of rotation of the cornea based on the pair of t_d_x 1260 and t_d_z 1235 or the pair of t_r_x 1270 and t_r_z 1245 as shown in FIG. 13.

$\varphi_{Eye\_X}$ means the angle at which the cornea rotates around the x-axis, and $\varphi_{Eye\_Z}$ means the angle at which the cornea rotates around the z-axis (see FIG. 9).

Accordingly, the processor 325 may determine the values of $\beta_M$ 1280 and $\Delta\beta_M$ 1290, and determine the angle of rotation of the cornea, that is, the direction of gaze, based on function of the angles $\varphi_{Eye\_X}$ and $\varphi_{Eye\_Z}$ of rotation of the cornea to track eye.

Figure 14:
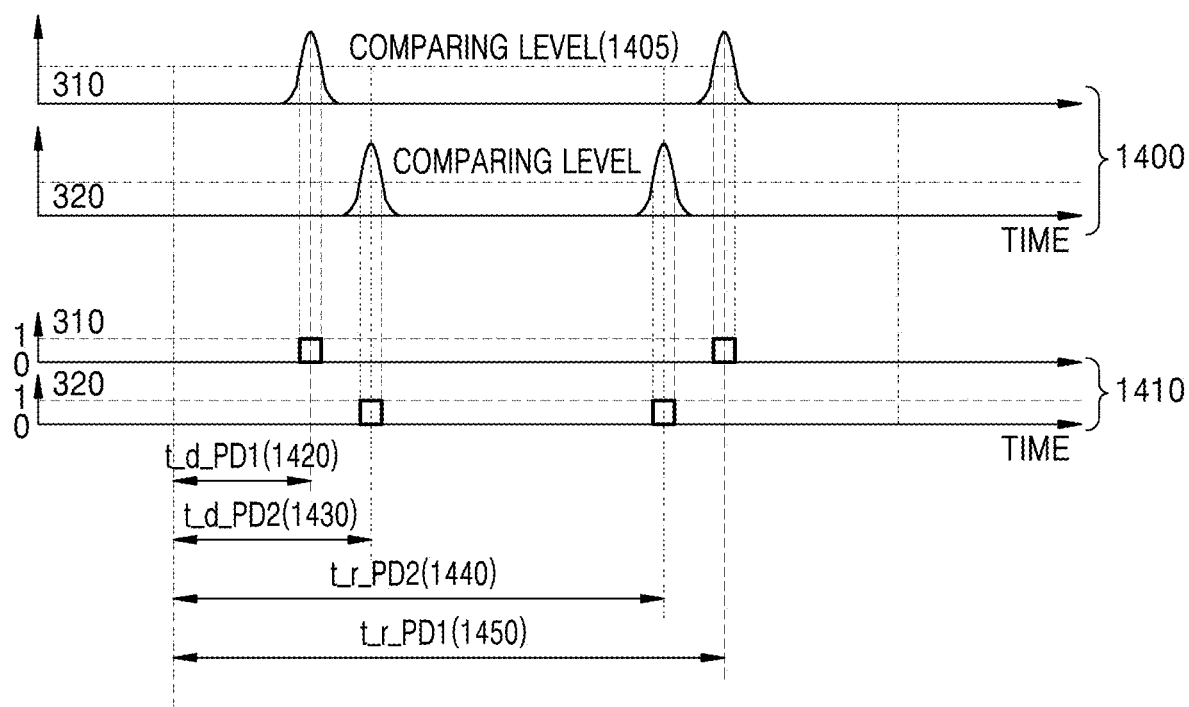
FIG. 14 is a diagram for describing an operation by which an eye-tracking electronic device digitizes an electric pulse according to an embodiment of the disclosure.

FIG. 14 is a diagram for describing an operation by which an eye-tracking electronic device digitizes an electric pulse according to an embodiment of the disclosure.

Referring to FIG. 14, a redundant configuration with FIG. 12 is briefly described.

Each of the photodetectors 310 and 320 may generate an electric pulse 1400 when a scanning line reflected from the cornea is incident. The electric pulse 1400 is generated by each of the photodetectors 310 and 320 when rotation of the position of the cornea occurs around the x-axis and the z-axis. That is, the position of the cornea freely moves.

The processor 325 may convert the electric pulse 1400 generated from each of the photodetectors 310 and 320 into a digital signal 1410. For example, the processor 325 may process the digital signal 1410 as 0 (zero) when the intensity of the electric pulse 1400 is lower than a comparison level 1405, and may process the digital signal 1410 as 1 (one) when the intensity of the electric pulse 1400 is higher than the comparison level 1405. However, the disclosure is not limited thereto, and the processor 325 may have various embodiments of the disclosure such as converting an analog signal into the digital signal 1410 using an analog-to-digital converter.

t_d_PD1 (time direct rotation photodetector 1) 1420, t_d_PD2 1430, t_r_PD1 (time reverse rotation photodetector 1) 1450 and t_r_PD2 1440 are respectively different from t_d_PD1 1220, t_d_PD2 1230, t_r_PD1 1250 and t_r_PD2 1240 in that the electric pulse 1210 is converted to the digital signal 1410. Accordingly, the processor 325 may determine the angle of rotation of the cornea based on t_d_PD1 1420, t_d_PD2 1430, t_r_PD1 1450, and t_r_PD2 1440.

Figure 15:
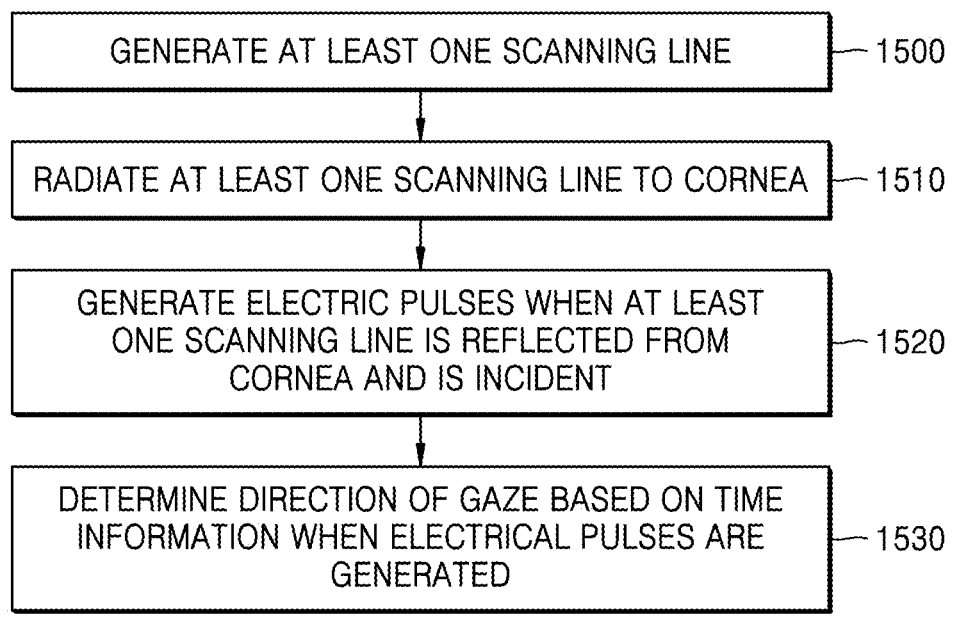
FIG. 15 is a flowchart of an operation, performed by an eye-tracking electronic device, of determining an angle of a cornea position according to an embodiment of the disclosure.

FIG. 15 is a flowchart of an operation in which an eye-tracking electronic device determines an angle of a cornea position according to an embodiment of the disclosure.

Referring to FIG. 15, in a direction of a gaze determining method, in operation 1500, the scanner 200 generates at least one scanning line. In operation 1500, the scanner 200 generates at least one scanning line including converting the scanning line to form a scanning area in the form of a line perpendicular to the scanning direction.

The scanner 200 may include the light source 210 and the optical element 220. Also, the scanner 200 may move the scanning area 410 through the rotation of the light source 210 and the optical element 220 or through the rotation of the single-axis scanner mirror 230.

In operation 1510, the scanner 200 radiates the scanning line to the cornea.

The scanning area moves through the rotation of the scanner 200. The rotation direction of the scanner 200 determines the scanning direction (DIRECT SCAN and REVERSE SCAN). The eye-tracking electronic device 300 may change the scanning direction at a certain period by determining a start point and an end point of scanning.

The eye-tracking electronic device 300 may increase (or decrease) the angle of rotation of the scanner 200 over time in various forms. Therefore, in consideration of a change in the position of the cornea, the processor 325 may accurately determine the direction of the gaze and increase the frequency of updating the direction of the gaze. For example, when the position of the cornea changes rapidly, the processor 325 rapidly increases (or decreases) the angle of rotation of the scanner 200 over time and slowly increases (or decreases) the angle of rotation of the scanner 200 near the position of the cornea, thereby quickly and accurately updating the direction of the gaze, for example, the position of the cornea.

In operation 1520, at least two photodetectors 310 and 320 generate electric pulses when the scanning line reflected from the cornea is incident. Each of the photodetectors 310 and 320 may detect the scanning line incident at a specific angle of rotation of the scanner 200 that satisfies the law of reflection. Accordingly, when the angles of rotation of the scanner 200 detected by the photodetectors 310 and 320 are used in combination with each other, information about the direction of the gaze may be obtained in one scan (or one period). That is, the frequency of updating information about the direction of the gaze may increase and the direction of the gaze may be more accurately determined.

In operation 1530, determine the direction of the gaze based on time information when the electric pulse is generated. In operation 1530, the direction of the gaze includes an operation of determining the angle of the cornea position.

The scanning line in the cornea may be partially reflected by being refracted or scattered. That is, all scanning lines reflected from the cornea may not be incident on the photodetectors 310 and 320. Therefore, because it is difficult to determine the direction of the gaze based on the intensity of the electric pulses generated by the photodetectors 310 and 320, there is a need to determine the direction of the gaze, for example, the angle of the cornea position, based on the generation time information of the electric pulse.

The eye-tracking electronic device 300 determines an angle at which the single-axis scanner mirror 230 rotates from a start time of scanning to an intermediate value of the formation time of the electric pulse generated by each of the photodetectors 310 and 320 based on the generation time information of the electric pulse.

The eye-tracking electronic device 300 determines an angle at which the single-axis scanner mirror 230 rotates during a time interval at which the maximum intensity of the electric pulse is generated by each of the photodetectors 310 and 320.

The eye-tracking electronic device 300 may express a function of the angle of rotation of the cornea based on the angle at which the single-axis scanner mirror 230 rotates and determine the angle of rotation of the cornea based on the function.

Figure 16:
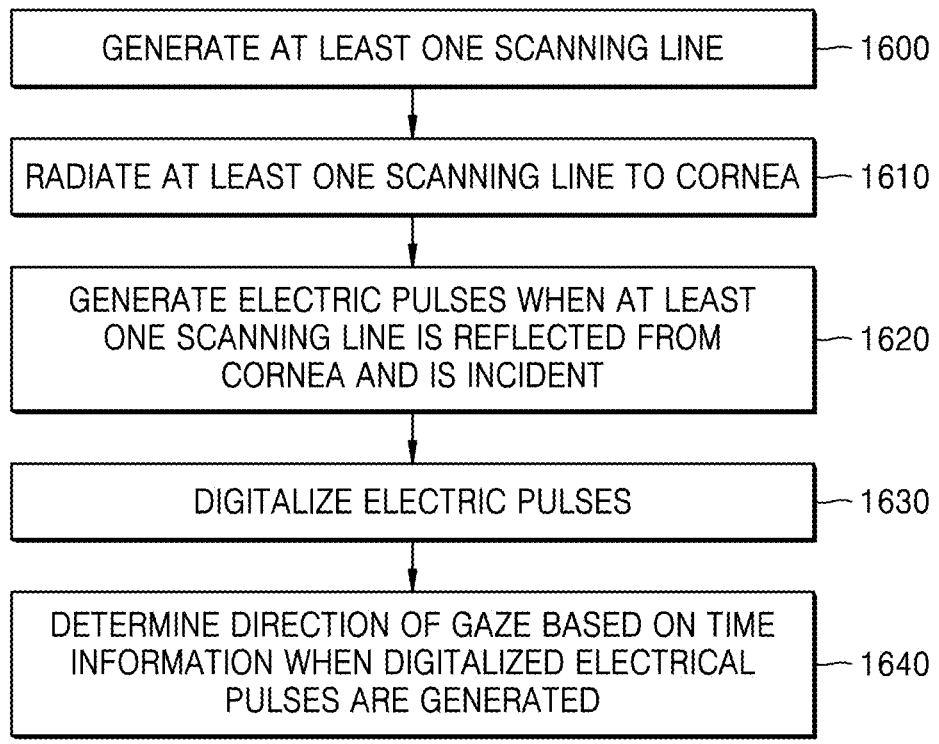
FIG. 16 is a flowchart of an operation, performed by an eye-tracking electronic device, of determining an angle of a cornea position according to an embodiment of the disclosure.

FIG. 16 is a flowchart of an operation in which an eye-tracking electronic device determines an angle of a cornea position according to an embodiment of the disclosure.

Referring to FIG. 16, a redundant configuration with FIG. 15 is briefly described.

In operation 1600, the scanner 200 generates at least one scanning line. In operation 1600, the scanner 200 generates at least one scanning line includes converting the scanning line to form a scanning area in the form of a line perpendicular to the scanning direction.

In operation 1610, the scanner 200 radiates the scanning line to the cornea.

In operation 1620, at least two photodetectors 310 and 320 generate electric pulses when the scanning line reflected from the cornea is incident. Each of the photodetectors 310 and 320 may detect the scanning line incident at a specific angle of rotation of the scanner 200 that satisfies the law of reflection.

In operation 1630, digitizing the electric pulse is performed. For example, when the intensity of the electric pulse is lower than a comparison level, a digital signal may be processed as 0, and when the intensity of the electric pulse is higher than the comparison level, the digital signal may be processed as 1 to thereby digitize the electric pulse. However, the disclosure is not limited thereto, and may provide various embodiments of the disclosure, such as converting an analog signal into a digital signal using an analog-to-digital converter.

In operation 1640, determine the direction of the gaze based on time information when the digitized electric pulse is generated. In operation 1640, the direction of the gaze includes an operation of determining the angle of the cornea position.

The eye-tracking electronic device 300 determines an angle at which the single-axis scanner mirror 230 rotates based on the time information when the electric pulse is generated. The eye-tracking electronic device 300 may express a function of the angle of rotation of the cornea based on the angle at which the single-axis scanner mirror 230 rotates and determine the angle of rotation of the cornea based on the function.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An eye-tracking electronic device comprising:
    a scanner;
    at least two photodetectors configured to generate electric pulses when a scanning line reflected from a cornea is incident thereon; and
    at least one processor configured to:
        generate at least one scanning line through the scanner,
        radiate the at least one scanning line to the cornea, and determine a direction of a gaze based on time information when the at least two photodetectors generate the electrical pulses, wherein the scanner comprises:
- a light source configured to generate the at least one scanning line;
- an optical element configured to convert the at least one scanning line to form a scanning area of a linear shape, having a length from an upper eyelid to a lower eyelid, perpendicular to a scanning direction; and
- a single-axis scanner mirror configured to rotate relative to one axis to move the scanning area.

2. The eye-tracking electronic device of claim 1, wherein the light source and the optical element each rotate around at least one axis.

3. The eye-tracking electronic device of claim 1, wherein the determining of the direction of the gaze comprises determining an angle of a position of the cornea.

4. The eye-tracking electronic device of claim 1, wherein the at least one processor is further configured to:
- digitalize the electric pulses, and
- determine the direction of the gaze based on time information at which the digitalized electric pulses are generated.

5. The eye-tracking electronic device of claim 4, wherein the at least one processor is further configured to digitalize the electric pulses by comparing the electric pulses with a set reference value.

6. The eye-tracking electronic device of claim 1, wherein the at least one processor is further configured to determine the direction of the gaze based on a time when the electric pulses are generated respectively by the at least two photodetectors and a generation time interval.

7. The eye-tracking electronic device of claim 1, wherein the at least one processor is further configured to determine the direction of the gaze based on a scanning speed of the scanner.

8. A method, performed by an eye-tracking electronic device, of determining a direction of a gaze, the method comprising:
- generating, by a scanner, at least one scanning line;
- radiating the at least one scanning line to a cornea;
- generating, by at least two photodetectors, electric pulses when the at least one scanning line is reflected from the cornea to be incident thereon; and
- determining the direction of the gaze based on time information when the electrical pulses are generated, wherein the scanner comprises:
- a light source configured to generate the at least one scanning line;
- an optical element configured to convert the at least one scanning line to form a scanning area of a linear shape, having a length from an upper eyelid to a lower eyelid, perpendicular to a scanning direction; and
- a single-axis scanner mirror configured to rotate relative to one axis to move the scanning area.

9. The method of claim 8, wherein the scanner comprises a light source and an optical element each configured to rotate around at least one axis.

10. The method of claim 8, wherein the determining of the direction of the gaze comprises determining an angle of a position of the cornea.

11. The method of claim 8, wherein the determining of the direction of the gaze based on the time information when the electrical pulses are generated comprises:
- digitalizing the electric pulses, and
- determining the direction of the gaze based on the time information when the digitalized electric pulses are generated.

12. The method of claim 11, wherein the digitalizing of the electric pulses comprises digitalizing the electric pulses by comparing the electric pulses with a set reference value.

13. The method of claim 8, wherein the determining of the direction of the gaze based on the time information when the electrical pulses are generated comprises determining the direction of the gaze based on a time when the electric pulses are generated respectively by the at least two photodetectors and a generation time interval.

14. The method of claim 8, wherein the determining of the direction of the gaze based on the time information when the electrical pulses are generated comprises determining the direction of the gaze based on a scanning speed of the scanner.

15. A computer program product comprising a non-transitory computer-readable recording medium having recorded thereon a program for executing a method, performed by an eye-tracking electronic device, of determining a direction of a gaze, the method comprising:
- generating, by a scanner, at least one scanning line;
- radiating the at least one scanning line to a cornea;
- generating, by at least two photodetectors, electric pulses when the at least one scanning line is reflected from the cornea and is incident thereon; and
- determining the direction of the gaze based on time information when the electrical pulses are generated, wherein the scanner comprises:
- a light source configured to generate the at least one scanning line;
- an optical element configured to convert the at least one scanning line to form a scanning area of a linear shape, having a length from an upper eyelid to a lower eyelid, perpendicular to a scanning direction; and
- a single-axis scanner mirror configured to rotate relative to one axis to move the scanning area.

* * * * *